United States Patent [19]

Anderson, II et al.

[11] Patent Number: 5,474,937
[45] Date of Patent: Dec. 12, 1995

[54] METHOD OF IDENTIFYING CHEMICALS BY USE OF NON-RADIOACTIVE ISOTOPES

[75] Inventors: David K. Anderson, II, Houston; Manuel E. Gonzalez; Nicholas P. Valenti, both of Kingwood, all of Tex.

[73] Assignee: Isotag, L.L.C., Houston, Tex.

[21] Appl. No.: 108,625

[22] PCT Filed: Jan. 25, 1993

[86] PCT No.: PCT/US93/00647

§ 371 Date: Aug. 30, 1993

§ 102(e) Date: Aug. 30, 1993

[87] PCT Pub. No.: WO93/15398

PCT Pub. Date: Aug. 5, 1993

[51] Int. Cl.$^6$ .................................................. G01N 33/24
[52] U.S. Cl. .................. 436/27; 436/3; 436/56; 436/60; 436/161; 436/139; 73/61.43; 73/61.44
[58] Field of Search ................................ 436/3, 27, 56, 436/60, 161, 139; 73/61.43, 61.44

[56] References Cited

U.S. PATENT DOCUMENTS

| | | | |
|---|---|---|---|
| 3,013,958 | 12/1961 | Fearon | 204/165 |
| 3,451,778 | 6/1969 | Fearon | 23/230 |
| 3,704,952 | 12/1972 | Bird | 356/87 |
| 3,788,814 | 1/1974 | Goldblatt et al. | 250/303 |
| 3,861,886 | 1/1975 | Meloy | 44/51 |
| 3,897,284 | 7/1975 | Livesay | 149/21 |
| 3,964,294 | 6/1976 | Shair et al. | 73/53 |
| 4,223,004 | 9/1980 | Hsia et al. | 424/9 |
| 4,242,186 | 12/1980 | Moran | 204/157.1 H |
| 4,251,726 | 2/1981 | Alvarez | 250/302 |
| 4,359,353 | 11/1982 | Kydd | 149/2 |
| 4,399,226 | 8/1983 | Danielson et al. | 436/56 |
| 4,441,943 | 4/1984 | Kydd | 149/109.4 |
| 4,469,623 | 9/1984 | Danielson et al. | 252/408.1 |
| 4,520,109 | 5/1985 | Simmonds et al. | 436/56 |
| 4,654,165 | 3/1987 | Fisenberg | 252/408.1 |
| 4,683,070 | 7/1987 | Munsell et al. | 252/33.4 |
| 4,690,689 | 9/1987 | Malcosky et al. | 48/174 |
| 4,731,531 | 3/1988 | Handke | 250/259 |
| 4,744,919 | 5/1988 | O'Holleran | 252/305 |
| 4,764,474 | 8/1988 | Orelup . | |
| 4,862,143 | 8/1989 | Hirshfield | 340/572 |
| 5,057,268 | 10/1991 | Muller | 376/157 |
| 5,111,882 | 5/1992 | Tang et al. | 166/252 |
| 5,179,027 | 1/1993 | Fisher | 436/56 |
| 5,246,861 | 9/1993 | Miller et al. | 436/27 |
| 5,256,572 | 10/1993 | Tang et al. | 436/27 |

OTHER PUBLICATIONS

"Subsurface Liquid Flow Tracing Enhanced by Los Alamos" Advanced Recovery Week, vol. 1, No. 37 (Nov. 12, 1990).
B. McInteer, et al., "The ICONS Facility": Separating Nitrogen and Oxygen Isotopes at Los Alamos, Los Alamos Tech. Bull. Mar., 1988 Isotag Brochure, Pub. Sep. 25, 1992.

*Primary Examiner*—David A. Redding
*Attorney, Agent, or Firm*—John R. Casperson

[57] ABSTRACT

A method is disclosed for identifying the source of a transported chemical shipment. The method employs either a chemical element or an organic compound with one or more atoms that are non-radioactive isotopes generally not found in nature. A small quantity of the isotopic compound is introduced into the storage vessel containing the chemical to be transported prior to shipment of the chemical. Upon arrival at its destination point, a sample of the chemical shipment is analyzed. Matching the isotopic compound found in the chemical with the isotopic compound introduced into the storage vessel prior to shipment is indicative that the shipped chemical is identical to the chemical received. Non-radioactive materials may further be employed for detecting the source of a newly introduced contaminant in a water supply. The chemical substance may be a non-radioactive isotope of the chemical shipment being transported.

11 Claims, No Drawings

METHOD OF IDENTIFYING CHEMICALS BY USE OF NON-RADIOACTIVE ISOTOPES

BACKGROUND OF THE INVENTION

Contamination of water with potentially hazardous materials is a common problem facing industry, the government and the general public. As a result of spills in waterways, leakage from storage facilities and surface discharges, contaminants are slowly destroying our water supply. Such contaminants may further enter our water supplies via subsurface soil and/or rock formations and eventually percolate into the groundwater. There are over two hundred organic and inorganic chemicals which have been identified in various groundwater supplies alone. Such ground water is the principal source of municipal water, agricultural irrigation, and water used by industry. There is thus a consistent health threat to our drinking water supplies. In addition, chemical discharging into intercoastal waters has resulted in damage to marine life as well as to marine ecosystems.

It is a fairly common occurrence to find such contaminants in our nation's lakes and rivers as well as the surrounding oceans. The amount of unlawful dumping of such wastes is increasing in the waters of the United States. Our groundwater, drinking water and waste water continues to be jeopardized as such activities continue. Useful methods of ascertaining the source of such pollutants into our waterways is essential.

Clearly there is a longfelt need by the public for a safe technique for "serializing" or "fingerprinting" petroleum, petroleum products and bulk chemicals in storage or transit so that responsibility for dumping, spilling or leakage of such chemicals can be appropriately determined. There is also a need for serializing bulk adulterants such as cyanides which are sometimes placed in foods and medicines by disturbed people to aid in apprehending such people. There is also a longfelt need by the petroleum and chemical industry for safe techniques to serialize oil and other chemical products for internally auditing the transfer of such products to prevent and/or prove theft.

It has been proposed to use radioactive materials as tracers in fluids. However, the use of radioactive materials for fingerprinting liquids would not be totally satisfactory. The consumption of petroleum products containing radioactive tracers, for example, would result in their uncontrolled release into the environment. It has also been proposed to use certain non-radioactive tracers in reservoir characterization studies to determine fluid residence times and conductive fluid flow paths. However, in such applications, the tracer is detected in salt water. Salt water is a very simple chemical composition and it is easy to obtain a low detection threshold because there are not many interfering materials. However, our proposals to label crude oil and other chemical materials with low levels of non-radioactive tagging agents have been met with skepticism because of the presumed difficulties in detecting such tagging agents. We have found that it is not difficult to identify many non-radioactive materials at very low levels if one knows what one is looking for.

SUMMARY OF THE INVENTION

It is an object of this invention to provide a method for identifying the source of a newly introduced contaminant in a water supply. The method employs a non-radioactive isotope of either a chemical element or an inorganic or organic compound. A small quantity of an isotopic compound is introduced into the storage container which further contains the environmentally harmful chemical. When spills of the chemical occur, a sample of contaminated water is recovered. The sample is then analyzed. Detection of the non-radioactive isotope in the contaminated sample is indicative of the source of the spill. The chemical substance may be a non-radioactive isotope of the chemical shipment being transported.

It is further an object of this invention to provide a method for identifying the source of a newly introduced contaminant in an oceanic water supply. Such contaminants appear in the water supply by either accidental or intentional dumping. Non-radioactive materials may further be employed for this method which has particular applicability in those cases where the substance being transported is environmentally toxic and hazardous. Prior to being loaded onto the cargo for transport, a non-radioactive material is introduced into the storage vessel containing the chemical. When spills of the transported chemical are suspected, a sample of the contaminant is recovered from the water supply and analyzed.

It is still further an object of this invention to provide a method for identifying the source of a transported chemical shipment at its destination port. The method employs a non-radioactive isotope of either a chemical element or an organic compound. A small quantity of the isotopic compound is introduced prior to shipment of the chemical into the storage vessel which further contains the desired chemical. Upon arrival at its destination point, the chemical shipment is analyzed. Matching the isotopic compound with the isotopic compound introduced into the storage vessel prior to shipment is indicative that the shipped chemical is identical to the chemical received. The chemical substance may be a non-radioactive isotope of the chemical shipment being transported. The method has particular applicability in the shipment of crude oil, refined oil, grains, processed and unprocessed chemicals, as well as bulk refined products.

In a further embodiment of the invention, there is provided a methods for labeling a fluid with an integral custody tag. The method is carried out by dispersing a detectable amount of the custody tag in the fluid. The custody tag is characterized in that it contains at least two tagging agents. When the tagging agents employed are selected from a moderately sized collection of tagging agents, the use of two or more tagging agents makes possible a very large number of unique custody tag possibilities.

In a further embodiment of the invention there is provided a method for analyzing a fluid to determine the identity of any tagging agents contained therein. The method is carried out by obtaining a sample of said fluid. The sample is converted into a chromatograph stream, such as by introduction into a gas chromatograph. The method is characterized in that a plurality of portions of the chromatograph streams are trapped and analyzed for the presence or absence of tagging agents. The method is further characterized in that the plurality of portions which are so trapped are predetermined. The predetermination is easily done when it is known that the tagging agents have been selected from a moderately sized collection of tagging agents. The portions of the stream which are trapped are simply those which may contain one of the constituents of the collection.

In a further embodiment of the invention, there is provided a chemical fluid which is labeled with an integral custody tag. The custody tag is characterized in that it is constituted by two or more tagging agents which are dispersed through said fluid at a combined concentration of less than 1 ppm.

In a further embodiment of the invention, there is provided a method of relabeling a fluid which is known to contain a custody tag comprising at least two tagging agents. The method comprises dispersing a custody tag modifier into said liquid to form a relabeled fluid. The custody tag modifier contains at least one tagging agent. Preferably, the tagging agent in the modifier is different from the two tagging agents in the liquid to be relabeled. By relabeling a liquid when it leaves one's custody or control, it will be easier to avoid liability if the fluid is subsequently dumped, spilled or leaked.

In a further embodiment of the invention, there is provided a method for a party to prove lack of responsibility for a material found at a dump, spill or leak site. The method comprises analyzing said material to obtain analysis results which identify the presence or absence of tagging agents in the material. Then, based on such analysis results, the party establishes either that said party never had custody of said material or that although said party had custody of said material at one time, such custody had been passed from said party to a transferee.

DETAILED DESCRIPTION OF THE INVENTION

The invention pertains to a method for identifying the source of a transported chemical shipment. The method may be employed to verify that a sample received by an individual is identical to the sample that was shipped. In addition, the invention may be employed to detect the source of a newly introduced contaminant in a source, such as a water supply.

The method employs a non-radioactive chemical isotope which, with the material being transported, is introduced into the storage container prior to the container being loaded onto a freight vessel. Either non-radioactive chemical elements or non-radioactive inorganic or organic compounds may be employed. The amount of isotopic compound introduced into the storage vessel may be less than one part per billion (ppb) of the chemical being transported. For certain isotopic compounds, the amount of isotopic compound introduced is between about 1 to about 5 ppb of the chemical being transported.

The invention finds particular applicability for marking chemical samples. Marking of the sample permits the recipient of the cargoed product to verify that the sample received is identical to the sample that was shipped. In this embodiment of the invention, the non-radioactive isotope substance is admixed with the chemical to be transported prior to shipment of the chemical. Upon arrival at its destination point, the chemical shipment is analyzed. Matching the isotopic compound with the isotopic compound introduced into the storage vessel prior to shipment is indicative that the shipped chemical is identical to the chemical received. The invention has applicability in the shipment of any chemical commodity, regardless of method of shipping or chemical structure of the commodity.

The method has particular applicability in the shipment of crude oil, refined oil, grains, processed and unprocessed chemicals as well as with bulk refined products. In addition, the invention may be employed in the shipment of a pollutant, hazardous material or a toxic material. As such, the invention has particular applicability in the identification of spilled shipments of spilled oil, pesticides, cyanide based compounds, arsenic containing compounds, dioxin, military chemical agents, military biological agents, naphthalene and biphenols.

The chemical substance may be a non-radioactive isotope of the chemical shipment being transported. Any element or compound which can be produced with stable isotopes not generally found in nature is suitable for the chemical substance. The substance is labeled with a non-radioactive atom at least one specific site in the molecule. Particularly preferred are those compounds deuterated or rendered isotopic by carbon-13 or fluorine-19. Also preferred are nitrogen-15, oxygen-17 and oxygen-18 isotopic materials.

The chemical substance is more commonly a non-radioactive isotope of such organic solvents as acetone, acetonitrile, benzene, bromobenzene, chlorobenzene, chloroform, cyclohexane, dichlorobenzene, trichloroethylene, diethylether, diglyme, dimethylsulfoxide, dioxane, ethanol, methanol, methylene chloride, nitrobenzene, octane, pyridine, tetrachloroethane, tetrahydrofuran, tetrametholsilane, toluene, trifluoroacetic acid, trifluoroethyl alcohol, xylene, ammonium bromide, or acetyl chloride.

Common inorganic deuterated solvents include deuterium oxide, ammonium deuteroxide, and deuterated ammonium sulfate. In addition, the non-radioactive isotope may be derived from an organometallic material. Isotopes of organometallic and inorganic compounds may include those containing iron-57, europium-15 1, and tin-119.

One particularly preferred class of organic compounds are those which have been deuterated, i.e., wherein the hydrogen atoms covalently bound to carbon atoms are replaced with deuterium atoms. Deuterium is a non-radioactive isotope of hydrogen which is often called heavy hydrogen. Deuteration of organic compounds can be accomplished by methods known in the art such as those disclosed in U.S. Pat Nos. 3,746,634 and 3,876,521 wherein deuteration is effected with deuterium gas in the presence of a Group VII or VIII metal catalyst at a temperature between about 100 and about 300 degrees C. The non-radioactive isotopes for use in this invention may further be prepared in accordance with the prior art teachings of such materials used in the medical arts.

The non-radioactive chemical substance may have the heavy atom in any position of the molecule. Likewise, one or more of the reactive sites of a molecule may contain a heavy atom. For example, the number of permutations possible with n-octane is in the thousands since one or all of the hydrogen atoms of the molecule may be substituted with deuterium as set forth below:

$CH_2DCH_2CH_2CH_2CH_2CH_2CH_2CH_3$;
$CH_3CHDCH_2CH_2CH_2CH_2CH_2CH_3$;
$CH_2DCHDCH_2CH_2CH_2CH_2CH_2CH_3$;
$CH_2DCH_2CH_2CH_2CH_2CH_2CH_2CH_2D$;
$CH_2DCHDCHDCH_2CH_2CH_2CH_2CH_3$;
$CH_2DCHDCHDCH_2CH_2CH_2CH_2CH_2D$.

The number of uniquely identifiable combinations of deuterated n-octanes naturally decreases the chance that more than one shipping vessel will contain the same non-radioactive isotope.

The method of this invention may further be employed for the identification of source of non-radioactive materials infiltrating water supplies. The method has particular applicability where the substance infiltrating the water supply is environmentally toxic and hazardous. By this process, a non-radioactive isotope of a chemical substance is introduced into a storage vessel containing the chemical supply to be transported prior to loading of the storage vessel onto the freight cargo leaving the exit port. When spills of the transported chemical are suspected, a sample of contaminated water is recovered from the water supply. The sample is then analyzed. Detection of the non-radioactive isotope in the contaminated sample is indicative of the source of the spill. The chemical substance may be a non-radioactive isotope of the chemical shipment being transported.

Suitable as the chemical substance used in the detection of the polluting source are those set forth above.

Still further the method of this invention may be employed to identify the source of chemical leakage from a land-based storage tank containing such a contaminant. The situs of the leakage may be either a water body or terrain. The presence of the contaminant is effectuated by recovering a sample of the contaminated area and analyzing the sample for the presence of the non-radioactive isotope to determine the location of the particular land-based storage tank which is leaking.

Isotopic identification may be readily achieved by mass spectroscopy, nuclear magnetic resonance spectroscopy or gas chromatography analysis. For instance, the spectra or retention time of the labelled isotope [prior to being introduced into the vessel containing the desired (ordered) chemical] may be compared to the spectra or retention time of the contaminant present in the water supply. See further B. B. McInteer et al., "The ICONS Facility: Separating Nitrogen and Oxygen Isotopes at Los Alamos", *Los Alamos Technical Bulletin*, March 1988.

In further embodiments of the invention, fluid compositions can be labeled or tagged by incorporating custody tag or custody tag modifiers therein. The fluid compositions are generally gases or liquids. The liquids are generally classified as oil based or water based. Oil based liquids generally include petroleum, and petroleum products. Volatile custody tags and custody tag modifiers are used to tag gases. Oil soluble custody tags and custody tag modifiers are generally used to tag oil based liquids. Water soluble custody tags and custody tag modifiers are generally used to label water based liquids. The custody tags are integral with the fluids and are nearly impossible to remove.

The amount of custody tag or tag modifier incorporated into the fluid can vary over a wide range. However, the tagging agent should always be added in an amount sufficient to be detected in the tagged product. Because the labeled fluids may be diluted a great deal with other materials before a sample is taken for analysis it can be desirable to incorporate a relatively large amount of custody tag into the fluid, although the amount used will generally be below about 1 ppm for economic reasons. On the other end of the scale, using current technology, certain tagging agents can probably be detected at levels of a few parts per trillion in gases and simple water solutions. The amount of custody tag employed in oil based liquids will generally be between these two ranges. Often, the custody tag will be used in an oil based liquid at below the 500 ppb level. In many instances, a concentration of custody tag in the range of 1 to 100 ppb will give desirable results.

The custody tag can be added to the fluid using a variety of techniques, depending on how well dispersion is expected. For example, the custody tag can be metered into a stream as it flows through a line. This will generally provide a better result than simply dumping the custody tag into a large storage tank, for example. However, an oil tanker can be treated by pouring the custody tag in the hold and then filling the tanker with oil. It is preferred to add the custody tag continuous to the fluid through a method system at a transfer or storage facility.

Generally speaking, a custody tag will comprise at least two tagging agents, preferably three or more. Custody tag modifiers comprise at least one tagging agent, preferably only one. A custody tag modifier can be used to relabel a fluid containing a custody tag to indicate, for example, a transfer of custody. Preferably, the tagging agent present in a custody tag modifier is different from any of the tagging agents in the custody tagged fluid being relabeled.

Tagging agents suitable for use can generally be described as non-radioactive compounds which are not naturally occurring and which are identifiable in tagged fluids at low thresholds of detection. Besides the tagging agents listed above, another example of suitable materials is the class of halogenated hydrocarbons, such as chlorinated and/or fluorinated alkenes, alkanes and aromatics. These materials are easily detected at low concentrations using gas chromatography techniques coupled with ion traps and/or mass spectrometer techniques. Preferably, the tagging agents used can be detected in the fluid which contains them at concentrations of less than 500 ppb, such as in the 1–100 ppb range. It is desirable to assemble a library or collection of suitable tagging agents and make selections from said library to formulate custody tags based on compatibility of the tagging agents with the fluid to be tagged and the use of a unique tag. Compatibility is rather easy to determine and is based on the range of properties of the fluid to be transported or stored. It does not require an especially large collection of tagging agents to accomplish the capability to provide unique combinations. For example, 1,000 tagging agents can be used to formulate over 41 billion unique 3-component custody tags. Where the goal is to police dumps, spills and leaks, a record should be made of the custody tags which have been assigned to individual companies or shipments. The records should be gathered or complied into a database. The database can be referred to in the event of a spill, leak or dump to assign responsibility.

The presently preferred analysis technique for the detection of tagging agents utilizes a gas chromatograph coupled with a mass spectrometer although other chromatographic techniques can be used as well. It is first necessary, of course, to obtain a sample of the material to be analyzed for the presence of tagging agents. The sample is formed into a gas chromatograph stream and the stream is then flowed through the gas chromatograph. Predetermined portions of the stream are trapped and analyzed for tagging agent. Generally speaking, the analysis is carried out with a mass spectrometer. For difficult separations, the trapped portions of the sample are formed into a second stream and flowed through a second gas chromatograph. Predetermined portions of the second gas stream are trapped and analyzed for tagging agent. The determination of which portions of the chromatograph stream to trap is generally made before the original analysis of the sample and is usually based on retention time. It is made using knowledge of the tagging agent collection from which the tagging agents were selected, sometimes after a calibration run using known combinations of tagging agents from the collection.

Besides product tracking, one of the more important uses of the invention is expected to be in proving the innocence of environmental wrongdoing. Suppose a company is suspected or accused of contributing to the amount of noxious materials present at the site of a dump, spill or leak. Proving lack of culpability would be much easier with the use of custody tags.

A sample of the material should first be obtained and then analyzed to determine whether any tagging agents are present. If no tagging agents were found, the company should be able to establish lack of culpability if it could show that it routinely used tagging agents during the time period in question. If tagging agents were found, the company should be able to establish lack of culpability if it used different tagging agents than those that were found, or if it required its transferees of the material to use the tagging agents that were found.

EXAMPLE 1

A 100,000 dead weight ton tanker is filled with crude oil for shipment to its desired location. About one eighth of one quart of deuterated octane of the formula $CH_2DCH_2CH_2CH_2CH_2CH_2CH_2CH_3$ is added to the crude oil. This provides approximately one part per billion of deuterated octane in the tanker. Upon arrival at its destination point, a sample of crude oil is removed from the tanker. Analysis by gas chromatography or mass spectroscopy indicates if the crude oil at the destination point is the same as the crude oil shipped from the origination port.

EXAMPLE 2

A 100,000 dead weight ton tanker is filled with crude oil for shipment to its desired location. About one eighth of one quart of deuterated acetone of the formula $CH_2DCOCH_2D$ is added to the crude oil. This provides approximately one part per billion of deuterated acetone in the tanker. A spill is located. A sample of the spill is removed and analyzed by either mass spectroscopy or gas chromatography. Matching of the data of the isotope $CH_2DCOCH_2D$ with the data from the spill will be determinative if the oil spill is attributed to the 100,000 dead weight ton tanker.

EXAMPLE 3

A 100,000 dead weight ton tanker is filled with crude oil for shipment from port A to its desired location, port B. About two and one-half quarts of a mixture of tetrafluoroethylene, chloroform, and trichloroethylene is added to the crude oil at port A. This provides approximately 20 parts per billion of halogenated hydrocarbon mixture in the oil. The ratio of tetrafluoroethylene:chloroform:trichloroethylene is 1:3:7.

A large spill of crude oil appears on the beaches of Galveston, Tex. and a sample is taken to identify the source of the crude oil spill. An analysis reveals that the crude oil contains one parts per billion of a mixture of tetrafluoroethylene, chloroform, and trichlorethylene in the ratio 1:3:7. Consequently, the spillage is conclusively identified as originating from the 100,000 dead weight ton crude oil tanker.

Having described the invention above, various modifications of the techniques, procedures, material and equipment will be apparent to those in the art. It is intended that all such variations within the scope and spirit of the appended claims be embraced thereby.

We claim:

1. A method for identifying the origin of a chemical fluid at a receipt location which comprises introducing into the chemical fluid at said origin at least one non-radioactive isotope of a chemical substance which will disperse in said chemical fluid and analyzing said chemical fluid at the receipt location for the presence of said at least one non-radioactive isotope, wherein said chemical substance comprises an organometallic material.

2. A method as in claim 1 wherein said non-radioactive isotope of the chemical substance has been labeled with a non-radioactive atom at least at one specific site in the molecules of the chemical substance.

3. A method for identifying the origin of a crude oil, refined oil, or bulk refined product at a receipt location which comprises introducing into said crude oil, refined oil or bulk refined product at said origin a combination of separately identifiable non-radioactive isotopes of chemical substances which will disperse in said crude oil, refined oil, or bulk refined product and analyzing said crude oil, refined oil or bulk refined product at the receipt location for the presence of said chemical substances.

4. A method for identifying the origin of a shipment of chemical fluid at a receipt location which comprises introducing into the shipment of chemical fluid at said origin a combination of separately identifiable non-radioactive isotopes which will disperse in said chemical fluid and analyzing said Shipment of chemical fluid at the receipt location for the presence of said non-radioactive isotopes.

5. A chemical fluid which is labeled with an a detectable amount of an integral custody tag, said custody tag comprising a unique combination of two or more separately identifiable tagging agents which are each dispersed in a detectable amount throughout said chemical fluid in a total concentration of less than 1 ppm each of said separately identifiable tagging agents comprising a chemical substance which has been labeled with a non-radioactive isotope.

6. A chemical fluid of claim 5 which is gaseous and contains less than 10 ppb of said custody tag.

7. A chemical fluid of claim 5 which is water based liquid and contains less than 100 ppb of said custody tag.

8. A chemical fluid of claim 5 which is oil based liquid and contains less than 500 ppb of said custody tag.

9. A chemical fluid as in claim 5 wherein the tagging agents contained in the custody tag are chemical compounds which are nonexistent in nature and can be identified in liquids using gas chromatograph/mass spectrometer techniques at concentrations in the range of 1 to 100 parts per billion, wherein said chemical fluid is in liquid form.

10. A chemical fluid as in claim 9 wherein the custody tag is non-radioactive and said chemical fluid is petroleum or a petroleton product, and said custody tag is uniquely selected frown a large number of custody tag possibilities based on a moderately sized collection of tagging agents.

11. A chemical commodity which is labeled with a detectable amount of an integral custody tag, said custody tag comprising a unique combination of two or more separately identifiable tagging agents which are each dispersed in a detectable amount throughout said chemical commodity in a total concentration of less than 1 ppm, each of said separately identifiable tagging agents comprising a chemical substance which has been labeled with a non-radioactive isotope.

* * * * *